United States Patent [19]

Anousis et al.

[11] Patent Number: 6,147,103
[45] Date of Patent: Nov. 14, 2000

[54] OMEPRAZOLE PROCESS AND COMPOSITIONS THEREOF

[75] Inventors: Nick Anousis; James W. McManus; Benjamin Newton Banks, all of Albany, Ga.; Lingwen Zhou, North Brunswick, N.J.

[73] Assignee: Merck & Co., Inc., Rahway, N.J.

[21] Appl. No.: 09/387,945

[22] Filed: Sep. 1, 1999

Related U.S. Application Data

[62] Division of application No. 09/169,231, Oct. 9, 1998.
[60] Provisional application No. 60/096,037, Aug. 11, 1998.

[51] Int. Cl.⁷ .................................................. A61K 31/415
[52] U.S. Cl. ............................................ 514/394; 514/395
[58] Field of Search ...................... 514/394, 395

[56] References Cited

U.S. PATENT DOCUMENTS

| | | | |
|---|---|---|---|
| 4,255,431 | 3/1981 | Junggren et al. | 424/263 |
| 5,386,032 | 1/1995 | Brändström et al. | 546/271 |
| 5,391,752 | 2/1995 | Hoerrner et al. | 546/271 |

FOREIGN PATENT DOCUMENTS

| | | |
|---|---|---|
| 0 484 265 A1 | 6/1992 | European Pat. Off. . |
| 0 302 720 B1 | 11/1992 | European Pat. Off. . |
| 539793 | 1/1985 | Spain . |
| 540147 | 2/1985 | Spain . |
| 550070 | 12/1985 | Spain . |
| 2239453 | 3/1991 | United Kingdom . |
| 96/38175 | 12/1996 | WIPO . |
| WO 98/40377 | 9/1998 | WIPO . |
| WO 98/40378 | 9/1998 | WIPO . |
| WO 98/09962 | 12/1998 | WIPO . |

*Primary Examiner*—Kevin E. Weddington
*Attorney, Agent, or Firm*—Philippe L. Durette; Melvin Winokur

[57] ABSTRACT

The present invention describes an improved process for the preparation, isolation, and purification of the anti-ulcer agent omeprazole whereby the sulfide precursor pyrmetazole is reacted subsurfacely with exactly one molar equivalent of meta-chloroperoxybenzoic acid in methylene chloride or toluene solution; residual organic solvent is removed from the aqueous layer by vacuum distillation; crude product is obtained by reactive crystallization with an alkyl formate and seeding; and pure product is isolated by recrystallization in methanol-water containing aqueous NaOH by subsurface addition of aqueous acetic acid to pH 9.0, seeding, filtration, washing, and drying. Compositions of omeprazole containing no chromatographically detectable levels of residual non-alcoholic organic reaction solvent are also described.

8 Claims, No Drawings

OMEPRAZOLE PROCESS AND COMPOSITIONS THEREOF

CROSS-REFERENCE TO RELATED APPLICATIONS

This application is a divisional of Ser. No. 09/169,231, filed Oct. 9, 1998, which in turn is related to U.S. provisional application Ser. No. 60/096,037 filed Aug. 11, 1998, the contents of which are hereby incorporated by reference.

FIELD OF THE INVENTION

The present invention provides a novel improved process for the preparation, isolation, and purification of the anti-ulcer agent omeprazole. Compositions of omeprazole containing no chromatographically detectable levels of residual non-alcoholic organic reaction solvent are also disclosed.

BACKGROUND OF THE INVENTION

Omeprazole, the generic name for 5-methoxy-2-[[4-methoxy-3,5-dimethyl-2-pyridinyl)methyl]sulfinyl]-1H-benzimidazole (denoted as Formula I below) is a well-described gastric proton-pump inhibitor and is on the market as LOSEC® or PRILOSEC® for the treatment of gastric and duodenal ulcers, gastritis, duodenitis, and reflux esophagitis (see Merck Index, 12th Ed., entry 6977, and references cited therein). Omeprazole is commercially prepared via a multi-step sequence, the last step of which is oxidation of the sulfide intermediate, 5-methoxy-2-[[4-methoxy-3,5-dimethyl-2-pyridinyl)methyl]methylthio]-1H-benzimidazole (denoted as Formula II below), known generically as pyrmetazole, which is typically effected with a peroxy acid, such as meta-chloroperoxybenzoic acid (hereinafter referred to as MCPBA) (U.S. Pat. Nos. 4,255,431 and 5,386,032), magnesium monoperoxyphthalate (MMPP) (U.S. Pat. No. 5,391,752), or peroxyacetic acid (WO 98/09962), in a suitable non-alcoholic organic reaction solvent. The preferred oxidizing agent is usually MCPBA, and suitable non-alcoholic organic reaction solvents include aromatic hydrocarbon solvents, such as benzene and toluene, and chlorinated aliphatic hydrocarbon solvents, such as chloroform and methylene chloride, in admixture with an alcoholic solvent, such as methanol, ethanol, isopropanol, or 1-butanol. The preferred non-alcoholic organic reaction solvents are usually methylene chloride and toluene, and the preferred alcoholic solvent is ethanol.

Prior processes to omeprazole have numerous disadvantages that limit both the yield and the purity of the final product.

A significant drawback of such prior methods is incomplete oxidative conversion of pyrmetazole into omeprazole as well as non-chemoselective oxidation. Two aspects of chemoselectivity are important in the oxidation of pyrmetazole. First, pyrmetazole contains two tertiary amino groups which can compete with the sulfide group for the oxidizing agent. Although these amino groups are less reactive than the desired sulfide, they can nevertheless undergo quantitative oxidation with MCPBA below ambient temperature. Second, the product omeprazole (a sulfoxide) can also react with MCPBA to form a sulfone by-product. Non-chemoselectivity and over-oxidation, characteristic of the previous methods, arise from ineffective control over the amount of the oxidizing agent as well as the manner in which the oxidizing agent is charged into the reaction vessel. Prior methods do not use accurately determined amounts of the oxidizing agent and do not provide for careful control of its addition to the reaction mixture. Non-chemoselective, over-, and under-oxidation all contribute to high impurities and loss of yield of the final desired product.

Another disadvantage of prior procedures is the considerable loss of product in the purification and isolation steps due to solubility of omeprazole in the mother liquors and solvent washes.

A further drawback concerns diminished product quality resulting from occlusion of residual solvents and reaction by-products during the crystallization steps. It is desirable to eliminate residual levels of organic reaction solvent and recrystallization solvent impurities in the final crystalline product for toxicity/safety reasons.

It is therefore an object of the present invention to provide an improved process for the preparation, purification, and isolation of omeprazole that overcomes the yield and product purity limitations of prior methods.

It is also an object of the invention to provide compositions of omeprazole having lower levels of residual non-alcoholic organic reaction solvent after the initial crude reactive crystallization step.

It is a further object of the present invention to provide final compositions of omeprazole that contain no residual non-alcoholic organic reaction solvent within the limits of chromatographic detection and less than 20 p.p.m. of residual crystallization solvent.

SUMMARY OF THE INVENTION

The present invention provides an improved process for the preparation, purification, and isolation of omeprazole of the Formula I.

The last chemical transformation in the preparation of omeprazole is the oxidative conversion of the sulfide intermediate pyrmetazole of the Formula II into its sulfoxide derivative omeprazole of the Formula I.

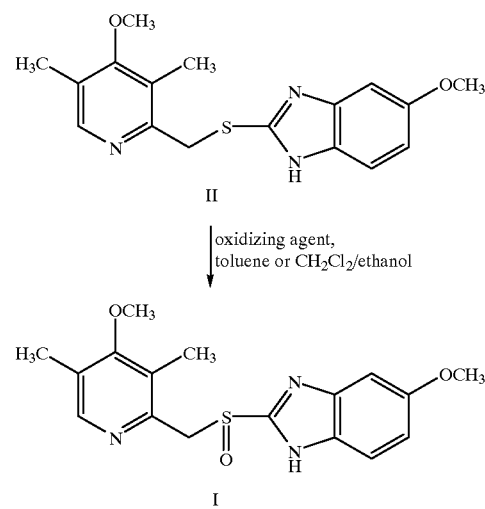

In one embodiment of the improved process, the oxidizing agent is meta-chloroperoxybenzoic acid (MCPBA), and the non-alcoholic organic reaction solvent is methylene chloride or toluene in admixture with an alcoholic solvent, such as methanol, ethanol, isopropanol, or 1-butanol, in particular, ethanol. In this embodiment, the completeness and chemoselectivity of the oxidation have been optimized by careful control of the amount of MCPBA charged to the reaction vessel. The use of one molar equivalent of MCPBA relative to the number of moles of pyrmetazole prevents non-chemoselective, over-, and under-oxidation resulting in fewer impurities and higher yields. In another embodiment of the present invention, the concentration of MCPBA in the charging solution is calculated using a novel analytical method based upon MCPBA oxidation of 3-methylisoquinoline to its N-oxide derivative and subsequent HPLC quantitation. Without this assay there exists no practical way to avoid either over-oxidation or incomplete conversion of pyrmetazole into omeprazole.

In a further embodiment of the present invention, control over localized over-oxidation is achieved by subsurface addition of MCPBA, providing for entry of the oxidizing solution into the reaction vessel at the tip of the agitator blades, with simultaneous control of the reaction temperature. Incorporation of these novel features into the process ensures complete conversion of pyrmetazole into omeprazole with no formation of sulfone by-products.

In another embodiment of the present invention, the isolation of the crude product has been improved by vacuum distillation of the crude aqueous phase after extraction of the reaction mixture prior to crystallization to remove most of the entrained methylene chloride or toluene from the oxidation step. The alcoholic solvent, in particular ethanol, concentration is re-adjusted in order to promote good crystal growth during the crude crystallization step. The crystallization step involves a two-stage neutralization with a $C_{1-3}$ alkyl formate, preferably methyl formate, which is added subsurfacely through a diptube located near and directed perpendicular to the impeller tip. This mode of addition of the methyl formate ensures rapid dispersion of the neutralizing agent, which promotes crystal growth over spontaneous nucleation. In so doing, occlusion of mother liquors in the crystals is minimized. Lowering the concentration of ammonia, relative to that used in prior procedures, in the ammonia-water wash, necessary to remove color impurities in the crude product, provides for further improvement in the yield of omeprazole.

A further embodiment of the present invention concerns the final purification step. A methanol-water mixture is used for the crystallization step which is initiated by subsurface addition of aqueous acetic acid and subsequent seeding with omeprazole. The same methanol-water mixture is employed as a displacement wash to remove mother liquors and dissolved impurities while suppressing solubility losses. In this fashion, significant yield improvements are obtained with no adverse impact on product quality.

Crystalline omeprazole is thus obtained with significant improvement in yield and purity. The isolated material contains no chromatographically detectable levels of residual non-alcoholic organic reaction solvent and less than 20 p.p.m. of residual methanol as the crystallization solvent.

BRIEF DESCRIPTION OF THE DRAWINGS

Not Applicable

DETAILED DESCRIPTION OF THE INVENTION

The instant invention relates to an improved process for the preparation, purification, and isolation of the proton-pump inhibitor omeprazole and to novel compositions thereof. Omeprazole, having formula I, is prepared by reacting a solution of pyrmetazole, having Formula II, cooled to about −5 to +5° C. and buffered to a pH of about 5 to 6,

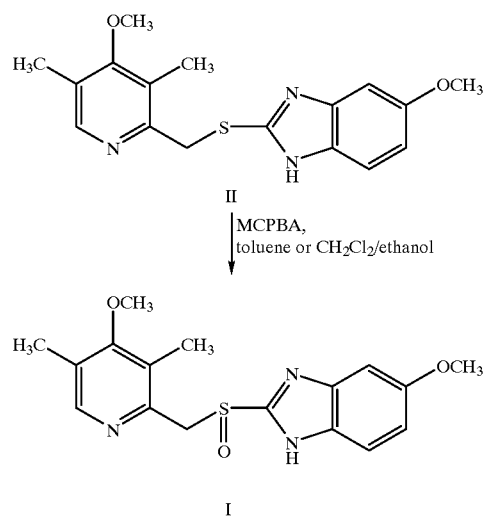

with one molar equivalent of an oxidizing agent, relative to the number of moles of pyrmetazole, dissolved in a non-alcoholic organic reaction solvent in admixture with an alcoholic solvent. The alcoholic solvent is selected from methanol, ethanol, isopropanol, and 1-butanol.

In one embodiment of the instant improved process, the buffered solution comprises potassium bicarbonate, the oxidizing agent is meta-chloroperoxybenzoic acid, and the non-alcoholic organic reaction solvent is methylene chloride or toluene, either in admixture with ethanol. The reaction is carried out such that both completeness and chemoselectivity of the oxidation are optimized. To force the reaction to proceed in a near quantitative fashion, it is necessary that any excess of the oxidizing agent, MCPBA, be minimized. Hence, the solution containing the oxidizing agent is accurately assayed so that an exact amount of reagent will be charged to the reaction vessel. In prior methods, the amount of MCPBA added was based on the commercial supplier's assay number. Since MCPBA solid contains about 15–25% water for safety reasons, the solid is not homogeneous. Therefore, the manufacturer can provide only the average assay results of MCPBA. If MCPBA from different containers and different suppliers is used, an inaccurate charge of MCPBA will result. A novel analytical method has therefore been developed to quantify MCPBA in the charging solution in order to deliver an accurate amount of the oxidizing agent. According to the assay, an excess amount of 3-methylisoquinoline (III) is reacted with CPBA in toluene/ethanol solution to form 3-methylisoquinoline N-oxide (IV), according to the equation:

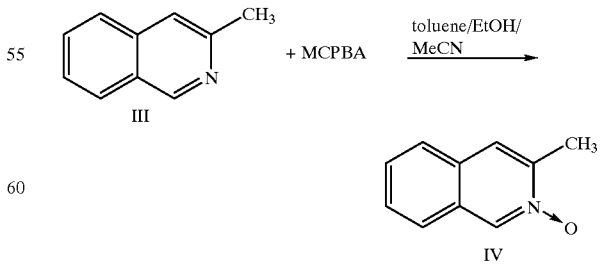

The reaction is fast and quantitative. The remaining tertiary amine in the reaction mixture is quantitated by reverse-phase high-performance liquid chromatography (RP-HPLC). The amount of the amine consumed during the reaction is used to calculate the concentration of the MCPBA solution.

It is also important that no excess oxidizing agent accumulate during addition of the reagent. This is best accomplished by subsurface addition of MCPBA, such that the solution enters the batch through a diptube located near and directed perpendicular to the agitator blades. This mode of addition provides for immediate dispersion of the oxidant, thus limiting localized over-oxidation.

Chemoselectivity and extent of oxidation are also enhanced by controlling the reaction temperature without crystallization of the oxidizing agent. The optimum temperature range is about 0–5° C. for the solution of the oxidizing agent and about −5 to +5° C. for the reaction mixture throughout the addition process. Higher temperatures of either the MCPBA solution or the reaction mixture will result in some sulfone formation. Likewise, much lower temperatures temporarily suppress the oxidation reaction, which results in a localized accumulation of the oxidizing a gent that can lead to over-oxidation products.

After addition of the solution containing the oxidizing gent, aqueous base, for example 50% NaOH or KOH, is added, the solution allowed to age for about 0.5–1.0 hours at 0–5° C., and the aqueous phase separated from the organic phase. To minimize residual levels of the non-alcoholic organic reaction solvent, in particular toluene or methylene chloride, in the crude product, which translates into higher levels of volatile non-alcoholic organic reaction solvent in the pure product, it is important to remove as much entrained toluene or methylene chloride as possible from the crude aqueous phase. The source of residual toluene or methylene chloride is an emulsion that forms when the crude batch is extracted from toluene or methylene chloride with aqueous base. Removal of residual solvent may be accomplished by vacuum distillation of the aqueous phase at a pressure of about 25–70 mm Hg and temperature of about 15–35° C. for about 1–4 hours. In further exemplification, the distillation is carried out at about 50 mm Hg and about 15° C. for 2 hours. The vacuum distillation procedure reduces the pre-crystallization levels of toluene or methylene chloride to less than 400 p.p.m. Other options to break up the emulsion and effect better phase separation are less effective; these include filtration of the crude aqueous phase through a bed of Celite™, increasing the settling time, and addition of a strong electrolyte.

Since the distillation process also results in removal of the alcohol, in particular ethanol, its concentration must be re-adjusted to approximately 15%, in order to facilitate crystal growth during the crude crystallization process. A lower level of the alcoholic solvent, in particular ethanol, produces finer crystals which are more likely to dissolve during subsequent washes thereby diminishing yields of the crude product.

At this point, the reactive crystallization of omeprazole is initiated and maintained under controlled conditions. Approximately 40% of a $C_{1-3}$-alkyl formate charge, preferably methyl formate, is added over the first 30 minutes to bring the batch from a pH of about 13.5 to near supersaturation at a pH of about 10.6 to 10.8. The methyl formate addition is accomplished through a diptube which is narrowed at one end to create a fine stream and which is located near and perpendicular to the impeller tip. This technique ensures rapid dispersion of the methyl formate so that occlusion of impurities is minimized. When a pH of about 10.6–10.8 is attained, the methyl formate addition is discontinued, and the batch is aged for ten to twenty minutes to allow the temperature to cool to approximately 20° C. prior to seeding. It is important to seed between pH 10.6 and 10.8. Below 10.6 spontaneous nucleation will occur with little crystal growth, if a sufficient seed bed is not present. Seeding is effected with pure, milled omeprazole (100% by HPLC), and the rest of the methyl formate is added subsurfacely over 6–8 hours to adjust the pH to about 9.0–9.3. This crystallization procedure improves both the yield and purity of the product. Without being held to a specific mechanism, it is believed that the purity enhancement is mainly due to preventing occlusion of mother liquors by promoting crystal growth over nucleation. Crude omeprazole at this stage contains less than 100 p.p.m. of residual toluene or methylene chloride, as determined by gas-liquid chromatographic analysis.

The crude crystallized product is then filtered, washed with 0.01–1.0%, preferably 0.1%, ammonia-water, and then methanol.

The crude wet omeprazole is then purified by dissolving it in 2:1–0.5–1 (v/v) methanol-water solution containing aqueous base, preferably 50% NaOH or KOH, at 20° C., cooling the basic solution to about 0–5° C., reducing the pH from >11.0 to approximately 10.5 by subsurface addition through a narrowed end diptube (configuration of apparatus same as in crude isolation step) of aqueous acetic acid, preferably 25% aqueous acetic acid, over a 30-minute period, while maintaining the temperature at 0–5° C. At this point the batch is seeded with pure omeprazole (100% by HPLC), and the subsurface addition of 25% aqueous acetic acid is continued over a 2–4 hour period until a pH of about 9.0 is attained. The batch is then aged for 0.5–1.0, preferably 0.5, hours. Following the aging period, the product is filtered, washed with the same methanol-water mixture to displace the mother liquors containing the impurities, and finally with cold methanol. Pure omeprazole is obtained after vacuum drying with a nitrogen purge at 30–50 mm Hg and 30–35° C.

The optimal methanol-water ratio in this final purification step is 1:1. Previous methods used a higher methanol to water ratio. Lowering the proportion of methanol in the solvent mixture used in the displacement wash minimizes solubility losses and provides the purification demands, thereby improving the yield of the final product without compromising product quality.

Crystalline omeprazole obtained using the improved process of the instant invention has an HPLC purity of 100% with no detectable levels of entrained residual toluene or methylene chloride from the crude step as measured by gas-liquid chromatography, the detection limit being 3 p.p.m. Prior methods have afforded omeprazole containing 30–100 p.p.m. of residual non-alcoholic organic reaction solvent, namely toluene or methylene chloride. The pure product contains less than 20 p.p.m. of residual methanol as the crystallization solvent.

For the preparation of pharmaceutical compositions in the form of dosage units for oral administration, omeprazole prepared according to the process of the present invention may be mixed with a solid, pulverulent carrier, such as lactose, saccharose, sorbitol, mannitol, starch, amylopectin, cellulose derivatives or gelatin, as well as an antifriction agent such as magnesium stearate, calcium stearate, and polyethyleneglycol waxes. The mixture is then pressed into tablets. If coated tablets are desired, the above-prepared core may be coated with a concentrated solution of sugar, which may contain gum arabic, gelatin, talc, titanium dioxide, or with a lacquer dissolved in volatile organic solvent or mixture of solvents. To this coating various dyes may be added in order to distinguish among tablets with different amounts of active compound present.

Soft gelatin capsules may be prepared which contain a mixture of pure omeprazole prepared according to the process of the present invention and vegetable oil. Hard gelatin capsules may contain granules of the active compound in combination with a solid, pulverulent carrier, such as lactose, saccharose, sorbitol, mannitol, potato starch, corn starch, amylopectin, cellulose derivatives, or gelatin.

Pharmaceutical tablets for oral use are prepared in the following manner. The solid substances are ground or sieved to a certain particle size, and the binding agent is homogenized and suspended in a suitable solvent. The solid omeprazole prepared according to the process of the present invention and auxiliary agents are mixed with the binding agent solution. The resulting mixture is moistened to form a uniform suspension having the consistency of wet snow. The moistening causes the particles to aggregate slightly, and the resulting mass is pressed through a stainless steel sieve having a mesh size of about 1 millimeter. The layers of the mixture are dried in carefully controlled drying cabinets for approximately ten hours to obtain the desired particle size and consistency. The granules of the dried mixture are sieved to remove any powder. To this mixture, disintegrating, antifriction, and antiadhesive agents are added. Finally, the mixture is pressed into tablets using a machine with the appropriate punches and dies to obtain the desired tablet size. The pressure applied affects the size of the tablet, its strength and ability to dissolve in water. The compression pressure used should be in the range of 0.5 to 5 tons. The tablets, especially those which are rough or bitter, may be coated with a layer of sugar or some other palatable substance. They are then packaged by machines having electronic counting devices.

The following examples illustrate the process of the present invention and are not intended to limit the scope of the invention set forth in the claims appended thereto.

EXAMPLE 1

HPLC Assay of MCPBA Charging Solution

Step A. HPLC Operating Parameters

High-performance liquid chromatography was performed using a Waters μBondapak C-18 column (4.6×300 mm, 10 μm particle size) with the following additional parameters:

Mobile phase: A=acetonitrile; B=0.1% $H_3PO_4$
Mode: isocratic 25%A/75%B at a flow rate of 1.0 mL/min
Injection size: 10 μL
Detector wavelength: 254 nm
Run time: 32 min.
Method of quantitation: Area by electronic integration
Approximate retention times: 3-methylisoquinoline: 3.5 mins.
3-methylisoquinoline N-oxide: 5.7 mins.
MCPBA: 11.4 mins.
Toluene: 25.1 mins.

| Step B. | Reagents | |
|---|---|---|
| | Acetonitrile (MeCN): | HPLC Grade |
| | Water: | HPLC Grade |
| | Phosphoric Acid: | HPLC Grade |
| | 3-Methylisoquinoline: | 98% |
| | Sample Diluent: | 50/50 (MeCN/0.1% $H_3PO_4$) |

Step C. Preparation of 3-Methylisoquinoline Standard

20±5 mg of 3-methylisoquinoline (98%) was transferred into a 10 mL volumetric flask and dissolved in 1.0 mL of MeCN. 1.0 mL of MCPBA after warming to room temperature was carefully pipetted into the flask, and the sides of the flask were washed with 1.0 mL of MeCN. The flask was then wrapped with parafilm and sonicated for 5 minutes. After cooling, the sides of the flask were washed with 1.0 mL of MeCN and the flask sonicated for an additional minute. The mixture was carefully diluted to the mark with acetonitrile. 1.0 mL of this solution was transferred by pipet to a 25-mL volumetric flask and diluted to the mark with the sample diluent from Step B.

Step D. Procedures

The HPLC system was equilibrated for at least 10 minutes at the mobile phase condition given in Step A. The standard preparation from Step C was injected twice, and the average area response for the 3-methylisoquinoline peaks should agree within ±1% of their average. The sample preparation was injected once.

Step E. Calculations

The concentration (mg/mL) of the MCPBA solution was calculated using the following equation:

$$\text{mg/mL of MCPBA solution} = (w - (A/As) \times Cs \times 250) \times \frac{172.57}{143.19}$$

where:

A=area response of the 3-methylisoquinoline for the Sample Solution

B=weight (mg) of the 3-methylisoquinoline in the Sample Preparation

As=average area response of the 3-methylisoquinoline for the Standard Solution

Cs=concentration of the 3-methylisoquinoline Standard Preparation 172.57=formula weight for 3-methylisoquinoline 143.19=formula weight for MCPBA As an illustration of the assay, an MCPBA sample from Spectrum (Lot# LF0102, 72.7% MCPBA) was assayed, and a value of 72.8% (wt. %) for MCPBA was obtained.

EXAMPLE 2

Preparation of Omeprazole with Methylene Chloride as Solvent

A solution of potassium bicarbonate (14.0 g, 0.140 mol, 1.2 equivalents) in deionized water (115 mL) was added to a solution of pyrmetazole (0.114 mol) in methylene chloride (170 mL) in a one-liter, three-necked round-bottom flask, and the mixture was cooled to 0° C. A solution of meta-chloroperoxybenzoic acid (MCPBA) (28 g, 0.114 mol, 1.0 equivalent) in methylene chloride (51 mL) and ethanol (13.3 mL) was prepared and assayed by the 3-methylisoquinoline/HPLC procedure described in Example 1 to ensure that exactly one molar equivalent of MCPBA is used. The solution is then cooled between 0–5° C. and added, subsurfacely directed at the tip of the impeller, to the rapidly agitated solution of pyrmetazole over a 2-hour period. The oxidation conversion was 99.8% with no over-oxidation to sulfone or N-oxides, as determined by HPLC analysis. Cold deionized water (115 mL, 5° C.) and 50% NaOH (15 mL) were then added to the reaction mixture. The solution was allowed to stand at 0–5° C. for thirty minutes and the phases separated. The methylene chloride layer was discarded and the aqueous layer concentrated under vacuum (50 mm Hg) for 2 hours at 15° C. to remove the bulk of the residual methylene chloride. The ethanol level was then re-adjusted to 15% v/v. At this point the residual methylene chloride level was less than 200 p.p.m., as determined by gas-liquid chromatographic analysis.

The crude product was then isolated by reactive crystallization by subsurface addition of methyl formate. Approximately 40% of the methyl formate charge (approximately 6 mL) was added during the first thirty minutes to adjust the pH from about 13.5 to 10.8. The mixture was allowed to stand for about twenty minutes to allow the internal temperature to cool back down to approximately 20° C. The mixture was seeded with pure omeprazole (0.5 g), and the remainder of the methyl formate (approximately 9 mL) was added subsurfacely over a 7-hour period to a pH of 9.0. The crude product was filtered, washed with 0.1% ammonia-water (50 mL) followed by methanol (40 mL).

The crude product was dissolved in 1:1 methanol-water (270 mL) and 50% NaOH (4 mL) in a 500-mL, three-necked, round-bottomed flask at 20° C. The solution was then cooled to 0–5° C. and the pH adjusted from >11.0 to approximately 10.5 by subsurface addition of 25% acetic acid over a 30-minute period, maintaining the temperature at 5° C. The batch was seeded with pure omeprazole (0.5 g), and the subsurface addition of 25% acetic acid was continued over a 4-hour period until pH 9.0 was achieved. After thirty minutes, the resulting solid was filtered, washed with 1:1 methanol-water (30 mL), and finally with cold (5° C.) methanol (30 mL). Pure omeprazole (100% as determined by HPLC analysis) was obtained after vacuum drying (50 mm Hg, 30–35° C.). The overall yield was 92.7%. The residual methanol level was 10 ppm, as determined by gas-liquid chromatography, with no detectable levels of methylene chloride (detection limit of 3 p.p.m.).

EXAMPLE 3

Preparation of Omeprazole with Toluene as Solvent

A solution of potassium bicarbonate (14.0 g, 0.140 mol, 1.2 equivalents) in deionized water (115 mL) was added to a solution of pyrmetazole (0.114 mol) in toluene (310 mL) in a one-liter, three-necked round-bottom flask, and the mixture was cooled to 0° C. Following the bicarbonate addition, a solution of meta-chloroperoxybenzoic acid (0.114 mol, 1 equivalent) in toluene (53 mL) and ethanol (20 mL) was assayed and charged to the pyrmetazole solution as in Example 2. The oxidation conversion was 99.8% with no over-oxidation to sulfone or N-oxides. Cold deionized water (145 mL, 5° C.) and 50% NaOH (12 mL) were then added to the reaction mixture. The solution was allowed to stand at 0–5° C. for thirty minutes and the phases separated. The toluene layer was discarded and the aqueous layer concentrated under vacuum (50 mm Hg) for 2 hours at 15° C. to remove the bulk of the residual toluene. The ethanol level was then adjusted to 15% v/v. At this point the residual toluene level was less than 400 p.p.m., as determined by gas-liquid chromatographic analysis.

The crude product was then isolated by reactive crystallization by subsurface addition of methyl formate as in Example 2. It was filtered, washed with 0.1% ammonia-water (50 mL) followed by methanol (40 mL). The wet crude product was then processed to pure omeprazole as in Example 2. The overall yield was 93.8% with an HPLC purity of 100%. The residual methanol level was 10 ppm, as determined by gas-liquid chromatography, with no detectable levels of toluene (detection limit 3 p.p.m).

EXAMPLE 4

A pharmaceutical composition containing omeprazole prepared according to the process of the present invention as the active ingredient is illustrated in the following formulation.

Capsules containing 30 mg of omeprazole of the present invention were prepared from the following ingredients:

| | |
|---|---|
| Compound of Example 2 or 3 | 300 grams |
| Lactose | 700 grams |
| Microcrystalline cellulose | 40 grams |
| Hydroxypropyl cellulose, low substituted | 62 grams |
| Disodium hydrogenphosphate | 2 grams |
| Purified water | q.s. |

The omeprazole of Example 2 or 3 was mixed with the dry ingredients and granulated with a solution of disodium hydrogenphosphate. The wet mass was forced through an extruder and sphreronized and dried in a fluidized bed dryer.

500 Grams of the pellets were coated with a solution of hydroxypropyl methylcellulose (30 grams) in water (750 mL) using a fluidized bed coater. After drying, the pellets were coated with a second coating as follows:

| | |
|---|---|
| Coating solution: | |
| Hydroxypropyl methylcellulose phthalate | 70 grams |
| Cetyl alcohol | 4 grams |
| Acetone | 200 grams |
| Ethanol | 600 grams |

The final coated pellets were filled into capsules.

What is claimed is:

1. A composition comprising 5-methoxy-2-[[4-methoxy-3,5-dimethyl-2-pyridinyl)methyl]sulfinyl]-1H-benzimidazole (omeprazole) having less than three parts per million of residual aromatic hydrocarbon solvent and less than 20 p.p.m. of residual methanol relative to omeprazole.

2. A composition comprising 5-methoxy-2-[[4-methoxy-3,5-dimethyl-2-pyridinyl)methyl]sulfinyl]-1H-benzimidazole (omeprazole) having less than three parts per million of residual chlorinated aliphatic hydrocarbon solvent and less than 20 p.p.m. of residual methanol relative to omeprazole.

3. The composition according to claim 1 wherein the aromatic hydrocarbon solvent is toluene.

4. The composition according to claim 2 wherein the chlorinated aliphatic hydrocarbon solvent is methylene chloride.

5. A pharmaceutical composition comprising 5-methoxy-2-[[4-methoxy-3,5-dimethyl-2-pyridinyl)methyl]sulfinyl]-1H-benzimidazole (omeprazole) having less than three parts per million of residual aromatic hydrocarbon solvent and less than 20 p.p.m. of residual methanol relative to omeprazole, and a pharmaceutically acceptable excipient.

6. A pharmaceutical composition comprising 5-methoxy-2-[[4-methoxy-3,5-dimethyl-2-pyridinyl)methyl]sulfinyl]-1H-benzimidazole omeprazole) having less than three parts per million of residual chlorinated aliphatic hydrocarbon solvent and less than 20 p.p.m. of residual methanol relative to omeprazole, and a pharmaceutically acceptable excipient.

7. The pharmaceutical composition according to claim 5 wherein the aromatic hydrocarbon solvent is toluene.

8. The pharmaceutical composition according to claim 6 wherein the chlorinated aliphatic hydrocarbon solvent is methylene chloride.

* * * * *

UNITED STATES PATENT AND TRADEMARK OFFICE
CERTIFICATE OF CORRECTION

PATENT NO. : 6,147,103  
DATED : November 14, 2000  
INVENTOR(S) : Nick Anousis, James W. Mc Manus, Benjamin Newton Banks, Lingwen Zhou Page 1 of 1

It is certified that error appears in the above-identified patent and that said Letters Patent is hereby corrected as shown below:

Claims,

Claim 1,
Lines 4-5, cancel "less than 20" and substitute therefor "10-20".

Claims 2, 5 and 6,
Line 5, in each, cancel "less than 20" and substitute therefor "10-20".

Signed and Sealed this

Sixth Day of November, 2001

*Attest:*

*Nicholas P. Godici*

NICHOLAS P. GODICI
*Attesting Officer*     *Acting Director of the United States Patent and Trademark Office*